United States Patent [19]

Alper et al.

[11] Patent Number: 4,694,097

[45] Date of Patent: Sep. 15, 1987

[54] CARBAMATE ESTER PRODUCTION

[75] Inventors: Howard Alper, Ottawa, Canada; David J. H. Smith, Camberley, England

[73] Assignee: The British Petroleum Company p.l.c., London, England

[21] Appl. No.: 856,665

[22] Filed: Apr. 25, 1986

[30] Foreign Application Priority Data

May 2, 1985 [GB] United Kingdom ............... 8511214

[51] Int. Cl.$^4$ .......................................... C07C 125/065
[52] U.S. Cl. .......................................... 560/24; 560/22; 560/25; 560/29; 560/30; 560/31; 560/32; 560/115; 560/157; 560/163
[58] Field of Search ............... 560/24, 132, 22, 25, 560/29, 30, 31, 32, 157, 163, 115

[56] References Cited

U.S. PATENT DOCUMENTS 4,251,667  2/1981  Kesling .......................... 560/24
4,260,781  4/1981  Harvey .......................... 560/24
4,297,501  10/1981 Becker et al. .................. 560/24

FOREIGN PATENT DOCUMENTS 0188557  11/1982  Japan .......................... 560/24

Primary Examiner—Michael L. Shippen
Attorney, Agent, or Firm—Brooks Haidt Haffner & Delahunty

[57] ABSTRACT

Carbamate esters are produced by reacting at ambient or elevated temperature an amine with carbon monoxide and an alcohol in the presence of a protonic acid, a dehydrating agent, for example a molecular sieve, and a catalyst comprising (a) at least one metal selected from the group palladium, rhodium, ruthenium, iridium and cobalt, and (b) at least one of the metals copper, molybdenum and iron, the components (a) and (b) being in the form of elemental metals or compounds thereof. The presence of the dehydrating agent reduces the formation of by-product carbon dioxide.

14 Claims, No Drawings

CARBAMATE ESTER PRODUCTION

The present invention relates to carbonylation reactions. In particular, the present invention relates to a process for the production of carbamate esters, otherwise known as urethanes, by the catalysed reaction of amines with carbon monoxide and an alcohol.

Carbamate esters are important molecules. They are generally prepared by reacting a chloroformate ester, itself obtained by reacting phosgene with an alcohol, with an amine or by reacting an isocyanate with an alcohol. Both phosgene and isocyanates are undesirable reactants from the point of view of toxicity and recent research has been directed to eliminating them from the production process.

Carbonylation reactions are well known. For example, processes for the production of carboxylic acids or esters by reacting an olefin with carbon monoxide and an alcohol in the presence of a base and a palladium/copper catalyst, optionally in the presence of oxygen are known. Furthermore, our pending European application publication No. 173457, published after the priority date claimed for the subject application but itself claiming an earlier priority date, describes a process for the production of carbamate esters by reacting an aromatic amine with carbon monoxide and an alcohol in the presence of a protonic acid and a catalyst comprising (a) at least one metal selected from the group palladium, rhodium, ruthenium, iridium and cobalt, and (b) copper. However, all of the conventional carbonylation processes which employ palladium/copper type catalysts produce excess carbon dioxide, a generally undesirable product.

It has now been found that the amount of by-product carbon dioxide generally associated with amine carbonylation reactions of the aforesaid type can be substantially reduced by operating the carbonylation process in the presence of a dehydrating agent.

Accordingly, the present invention provides a process for the production of a carbamate ester which comprises reacting at ambient or elevated temperature an amine with carbon monoxide and an alcohol in the presence of a protonic acid, a dehydrating agent and a catalyst comprising (a) at least one metal selected from the group palladium, rhodium, ruthenium, iridium and cobalt, and (b) at least one of the metals copper, molybdenum and iron, the components (a) and (b) being in the form of elemental metals or compounds thereof.

The amine may suitably be either an aromatic, an aliphatic or a cycloaliphatic amine, preferably an aromatic amine. The aromatic amine may suitably be a compound wherein one or more amine groups are connected to one or more aromatic rings. For example, the aromatic amine may suitably be aniline or a derivative thereof, an aminotoluene, a diarylamine, a phenylene diamine (benzene diamine) or the like. Suitable derivatives of aniline include the alkyl substituted, for example toluidines and xylidenes, the alkoxy substituted, for example anisidines, phenetidines and cresidines, the haloanilines, for example chloroanilines and nitroanilines. Preferred aminotoluenes are the diaminotoluenes, of which the 2,4- and 2,6-isomers, or mixtures thereof, are particularly preferred. A suitable phenylene diamine is 4,4'-methylene dianiline. Suitably the aliphatic amine may be an alkylamine, for example n-propylamine, t-butylamine or di-n-butylamine.

The carbon monoxide may be provided by any suitable source and may contain other gases such as carbon dioxide, hydrogen and light hydrocarbons in small amounts. The carbon monoxide pressure may suitably be the autogenous pressure at the reaction temperature employed. Alternatively, elevated pressures, suitably in the range from 2 to 250 psig above the autogenous pressure at the reaction temperature may be employed.

As regards the alcohol reactant, monohydric and polyhydric alcohols may be employed. Suitable alcohols may be represented by the formula $R_2CHOH$ wherein R is independently hydrogen, alkyl, hydroxyalkyl, or aryl or two R groups may bond together to form a ring. Preferably, the alcohol is an alkanol, for example methanol, ethanol, a propanol or a butanol.

The aforesaid reactants, ie the amine, carbon monoxide and alcohol, are preferably employed in substantially anhydrous form.

The protonic acid may be either a mineral acid, or an organic acid which may suitably be a carboxylic acid. Suitable acids include sulphuric acid, hydrochloric acid and acetic acid. Alternatively, the protonic acid may be supported on an inert support, or may be a solid acid, for example an ion-exchange resin in the acid form.

With regard to the catalyst, one or more of the metals palladium, rhodium, ruthenium, iridium and cobalt is employed as component (a). The metal(s) may be in the form of the elemental metal(s), such as a finely divided powder, or in the form of a compound of the metal(s). Suitable compounds of the metal(s) include salts of the metals such as chlorides, iodides, acetates and nitrates, preferably the chlorides. Preferably the metal is palladium, suitably in the form of palladium (II) chloride.

Component (b) of the catalyst is preferably copper which may suitably be added in the form of a cuprous or a cupric compound or as a mixture thereof. A wide variety of copper compounds may be used in the process of the invention. Examples of suitable copper compounds include copper (I) acetate, copper (II) acetylacetonate, copper (I) bromide, copper (I) chloride, copper (II) chloride, copper (I) iodide, copper (II) nitrate, and the like.

With regard to the ratios of the metal catalyst components, the molar ratio of copper component (b) to metal(s) component (a) may suitably be in the range from 1:1 to 200:1, preferably from 2:1 to 50:1.

The molar ratio of amine to the metal(s) component (a) may suitably be in the range from 5:1 to 1000:1, preferably from 10:1 to 250:1.

Also present in the reaction mixture is a dehydrating agent. The dehydrating agent can be any material which will react with or absorb water but will not react with the starting reactants including but not limited to ortho-formates, carboxylic acid anhydrides and molecular sieves. The preferred dehydrating agents are molecular sieves which may suitably be coated, impregnated or otherwise bonded by conventional techniques with, or physically mixed with, the metal components of the catalyst. Most preferred are the type A zeolites such as 3A, 4A or 5A zeolites which are commercially available. The most preferred type A zeolites are 3A type zeolites which can contain the potassium cation.

The molecular sieve should be present in an amount from 1% to 100%, by weight based on the weight of the amine starting reactant.

Oxygen may be present or absent. However, it is preferred to operate in the presence of oxygen because by doing so the product yields can generally be improved. Oxygen may be supplied to the reaction either as essentially pure oxygen or admixed with other gases which are substantially inert under the reaction conditions. Air may conveniently be used as the source of oxygen. The oxygen pressure may suitably be the autogenous pressure at the reaction temperature employed. Alternatively elevated pressures may be employed if desired.

A supplemental diluent which is capable of forming a second liquid phase, the first liquid phase being formed by the alcohol, may be employed. The particular diluent employed should be inert under the reaction conditions and should be substantially insoluble in the alcohol phase. Suitably the diluent may be an aliphatic hydrocarbon, a cycloaliphatic hydrocarbon, an aromatic hydrocarbon, an alkyl-substituted aromatic hydrocarbon or a halogenated aliphatic or aromatic hydrocarbon. Examples of suitable diluents include benzene, toluene, hexane, cyclohexane, chlorobenzene, bromobenzene, a xylene, dichloromethane, chloroform and 1,2-dichloroethane. It will be appreciated by those skilled in the art that the organic solvent should be chosen with regard to the difference in boiling points between the products of the reaction and the diluent so as to facilitate separation of the reaction mixture into its individual components.

The amount of alcohol and supplemental diluent phase based on the amine reactant can vary over a wide range, suitably from 20 to 0.2, preferably from 5 to 1, volumes of supplemental diluent per volume of amine reactant and from 20 to 0.2, preferably from 5 to 1 volumes alcohol per volume of amine reactant.

The process may suitably be operated at ambient temperature, though elevated temperatures, for example in the range 20° to 150° C. or even higher may be employed. The reaction time may vary over a wide range, suitably from about 30 minutes to 8 hours, though longer reaction times may be employed if desired.

The process may be carried out batchwise or continuously.

The invention is further described with reference to the following Examples. However, these Examples have been provided merely to illustrate the present invention and should not be construed as limiting the scope of the invention which includes equivalent modifications, variations and embodiments.

EXAMPLE 1

A mixture of p-toluidine (p—$CH_3C_6H_4NH_2$) (10 mmol), $PdCl_2$ (1 mmol), $CuCl_2$ (2 mmol), methanol (60 ml), glacial acetic acid (0.1 ml), and 3A molecular sieve (3 g) was stirred overnight at room temperature and under 1 atm. pressure. During this time, carbon monoxide and oxygen were bubbled through the solution. The amount of carbon dioxide which evolved during the reaction was determined by bubbling the gases through a saturated solution of barium hydroxide. Work-up gave 88% of the carbamate ester (p—$CH_3C_6H_4NHCOOCH_3$) and 0.08 mmol of $CO_2$ was formed per 10 mmol of substrate.

Comparison Test

The procedure of Example 1 was repeated except that the 3A molecular sieve was omitted.

Only 68% of the carbamate ester was obtained and 14 mmol of $CO_2$ were produced per 10 mmol of amine.

EXAMPLE 2

The same procedure as used in Example 1 was applied to dodecylamine and t-butanol affording $C_{12}H_{25}$—$NHCOOC(CH_3)_3$ in 75% yield in this solution. In this reaction, 1.0 mmol of $CO_2$ was evolved per 2.0 mmol of substrate.

EXAMPLE 3

The procedure of Example 1 was repeated except that $(CH_3)_3CNH_2$ was used in place of p-toluidine.

$(CH_3)_3CNHCOOCH_3$ was obtained in 98% yield.

EXAMPLE 4

The procedure of Example 3 was repeated except that methanol was replaced by $(CH_3)_3COH$.

$(CH_3)_3CNHCOOC(CH_3)_3$ was obtained in 60% yield.

EXAMPLE 5

The procedure of Example 1 was repeated except that 2,5-$(CH_3)_2C_6H_3NH_2$ was used in place of p-toluidine.

2,5-$(CH_3)_2C_6H_3NHCOOCH_3$ was obtained in 70% yield.

EXAMPLE 6

The procedure of Example 1 was repeated except that di-n-butylamine ($Bu_2NH$) was used in place of p-toluidine and the protonic acid was hydrochloric acid.

Both $Bu_2N.CO.CO.OCH_3$ and $Bu_2NCOOCH_3$ were obtained, the latter being the main product.

EXAMPLE 7

The procedure of Example 1 was repeated except that p—$ClC_6H_4NH_2$ was used in place of p-toluidine.

p—$ClC_6H_4NHCOOCH_3$ was obtained in 61% yield.

EXAMPLE 8

The procedure of Example 1 was repeated except that m—$CH_3COC_6H_4NH_2$ was used in place of p-toluidine.

m—$CH_3COC_6H_4NHCOOCH_3$ was obtained in 99% yield.

EXAMPLE 9

The procedure of Example 1 was repeated except that n—$C_3H_7NH_2$ was used in place of p-toluidine.

n—$C_3H_7NHCOOCH_3$ was obtained in 98% yield.

We claim:

1. A process for the production of a carbamate ester which process comprises reacting at ambient temperature or elevated temperature in the range 20° to 150° C. an amine with carbon monoxide and an alcohol in the presence of a protonic acid, a dehydrating agent and a catalyst comprising (a) at least one metal selected from the group of palladium, rhodium, ruthenium, iridium and cobalt, and (b) the metal copper, the components (a) and (b) being in the form of elemental metals or compounds thereof.

2. A process according to claim 1 wherein the amine is either an aromatic, aliphatic or cycloaliphatic amine.

3. A process according to claim 1 wherein the amine is an aromatic amine which is either aniline, an aniline derivative, an aminotoluene, a diarylamine or a phenylene diamine.

4. A process according to claim 1 wherein the alcohol is an alkanol.

5. A process according to claim 1 wherein the protonic acid is a carboxylic acid.

6. A process according to claim 1 wherein component (a) of the catalyst is palladium.

7. A process according to claim 1 wherein the dehydrating agent is a molecular sieve.

8. A process according to claim 7 wherein the molecular sieve is a type A zeolite.

9. A process according to claim 8 wherein the type A zeolite is a 3A-type zeolite.

10. A process according to claim 1 when operated in the presence of oxygen.

11. A process according to claim 1 wherein the amine is an aromatic amine.

12. A process according to claim 1 wherein the amine is an aliphatic amine.

13. A process according to claim 1 wherein the amine is a cycloaliphatic amine.

14. A process according to claim 1 wherein the temperature is in the range of 20° C. to room temperature.

* * * * *